United States Patent [19]
Barrington

[11] 3,986,508
[45] Oct. 19, 1976

[54] STERILIZABLE, MEDICAL CONNECTOR FOR BLOOD PROCESSING

[75] Inventor: James E. Barrington, Hingham, Mass.

[73] Assignee: Abcor, Inc., Cambridge, Mass.

[22] Filed: Nov. 6, 1974

[21] Appl. No.: 521,253

Related U.S. Application Data

[63] Continuation-in-part of Ser. No. 390,506, Aug. 22, 1973, abandoned.

[52] U.S. Cl................................ 128/214.2; 222/83; 285/3
[51] Int. Cl.²............................................ A61M 5/00
[58] Field of Search......... 128/214 R, 214.2, 214 C, 128/214 D, 215, 272; 285/3, 260; 137/68; 141/329, 330; 222/80–83

[56] References Cited
UNITED STATES PATENTS

| | | | |
|---|---|---|---|
| 2,847,995 | 8/1958 | Adams | 128/214 R |
| 2,933,333 | 4/1960 | Bredtschneider | 285/3 |
| 3,127,892 | 4/1964 | Bellamy et al. | 128/214.2 |
| 3,171,412 | 3/1965 | Braun | 128/214 D |
| 3,865,411 | 2/1975 | Rowe et al. | 285/363 |
| 3,902,489 | 9/1975 | Carter | 128/214 R |

FOREIGN PATENTS OR APPLICATIONS

| | | | |
|---|---|---|---|
| 1,373,027 | 8/1964 | France | 128/214.2 |
| 1,300,635 | 8/1969 | Germany | 128/214 R |

*Primary Examiner*—Dalton L. Truluck
*Attorney, Agent, or Firm*—Richard P. Crowley

[57] ABSTRACT

A two-stage, sterilizable connector for use in processing blood, which connector assures sterility when entering a blood bag to add agents required in processing blood, the connector designed to comprise a male and female body element which, in a first extended position, are partially joined, which connector is sterilizable, and which, after sterilization, the male and female body elements are joined in a secured, engaged position to effect the puncturing of the male and female septa to provide a fluid passageway therethrough.

36 Claims, 13 Drawing Figures

STERILIZABLE, MEDICAL CONNECTOR FOR BLOOD PROCESSING

REFERENCE TO PRIOR APPLICATION

This application is a continuation-in-part of application Ser. No. 390,506, filed Aug. 22, 1973 (now abandoned).

BACKGROUND OF THE INVENTION

Present techniques for providing for entry into a sterile system, such as to permit the penetration of a blood bag through the entry of agents into a blood bag, depend upon the puncture of a diaphragm by a hollow needle. Typically, both the male and female sections of the coupling are covered in order to preserve sterility up to the time that the connection is made. Nevertheless, in order for the connection to be made, typically the protective cover must be removed, exposing the surfaces. Such exposure, however brief, introduces the possibility of contamination to the sterile surfaces. Thus, present techniques used in blood connectors do not assure sterility in entering a blood bag to add agents required in the processing of blood for freezing. Therefore, there exists a need for a connector designed so that it may assure sterility in a sterile seal prior to use in entering a blood bag.

SUMMARY OF THE INVENTION

My invention concerns a sterilizable connector and a new closure method which permits a blood bag system to be entered dand assures sterility. In particular, my invention relates to a two-stage, sterilizable, male-female connector whereby all surfaces exposed during the coupling operation may be sterilized before the blood bag or other system is actually entered. More particularly, my invention is directed to a two-stage chemical, heat or radiation-sterilizable male-female connector and technique which permits and assures sterility when entering a blood bag to add agents required in processing blood for freezing.

My connector is so designed that it, in its extended position, is partially joined without breaking the sterile seal into the blood bag system referred to as a first extended-stage assembly of a connector. The connector in such first stage is then sterilized, such as by heat sterilization by a matching sterilizer, to remove any contamination reaching the exposed surfaces during the connection. After sterilization, the male and female body elements of my connector are then completely joined by moving the male and female body elements toward each other into a final stage or engaged position to join the septa surfaces and to permit a needle to puncture the male and female septa, opening a fluid passageway between the separate elements. Since my connector, in its engaged stage, is joined together while within the confines of the sterilizer, there is no possibility of the sterile mating surfaces becoming contaminated after sterilization, thereby permitting my connector to be used to enter a blood bag or other system where sterility of the connection is desired.

DESCRIPTION OF THE EMBODIMENTS

FIGS. 1–6 show a connector 10 comprising a male body 12 and a female body 14 typically composed of an inert thermoplastic material, preferably one which is heat-resistant and sterilizable at temperatures above 300° F where the connector is to be heat-sterilizable, and typically a plastic material which may be easily mold-injected. Such material should maintain its structural integrity at temperatures up to about 400° F, such as a polyethylene haloethylene like polytrifluoroethylene material known as KEL-F, a registered trademark of 3-M Company, a polyamide or a polyarylsulfone resin. The female and male body elements 12 and 14 are adapted as shown more particularly in FIG. 5 to be engaged in a first extended stage of union, generally for illustration purposes with a gap between ends of the elements. The tubular male body element 12 comprises a tapered portion 18 which is adapted to accept and be connected to plastic tubing, while the main body element 20 is composed of a knurled grasping portion for the user, a first tubular inset portion 22 and an extending second insert tubular portion 24. A passageway 26 extends from one to the other end of the male body 12, with a male septum element 28 composed of a puncturable resilient material, such as a biomedically acceptable material like silicone rubber, and adapted to fit over the tubular portion 24 at the closed end of the male body element 12. Typically, the septum should be molded from a material which has biocompatibility and which is resistant to high temperatures or to the particular sterilizing techniques to be employed with the connector.

Figure 1:
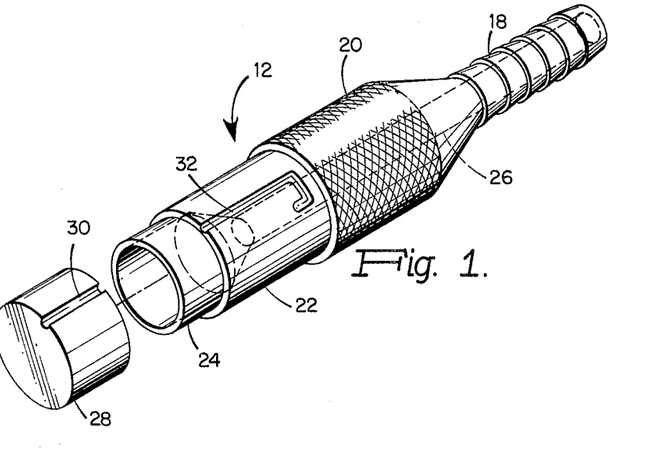
FIG. 1 is a perspective partially exploded view of the male element of my connector.
Figure 2:
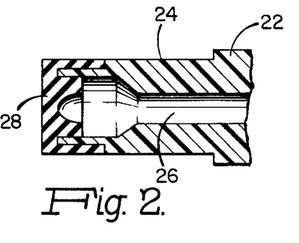
FIG. 2 is an enlarged cross-sectional fragmentary view of one end of the male element of the connector.

As illustrated, the male septum 28, as shown more particularly in FIG. 2, is in a cap-like or E-shape form with the tubular portion 24 inserted therein, the exterior surfaces of the tubular portion being sealingly engaged with the inset of the male septum 28. The external surface portion of the male body element 12, particularly tubular portion 22, and the male septum 28 contains and is designed to provide a means for retaining the male and female elements together when placed in a matingly engaged position, such as a longitudinally axially extended vent and bayonet clasp channel 30 in the septum and 32 in the tubular portion 22. As shown and illustrated, the male septum 28 hanging over the front end of the plastic body element 12 slides with it into a first and later engaging positions with the female body element 14.

Figure 3:
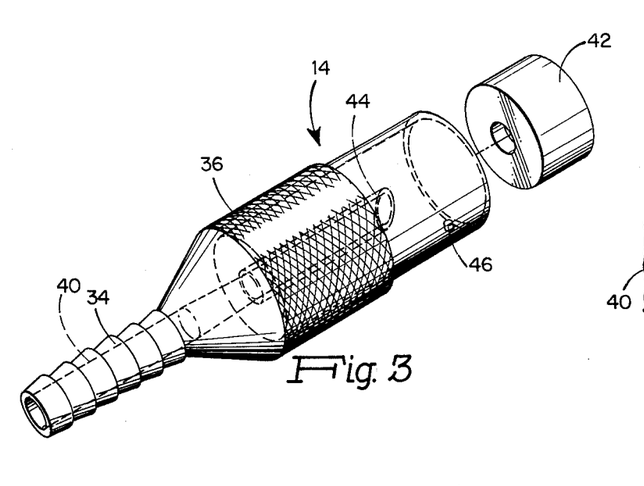
FIG. 3 is a perspective partially exploded view of the female element of the connector.
Figure 4:
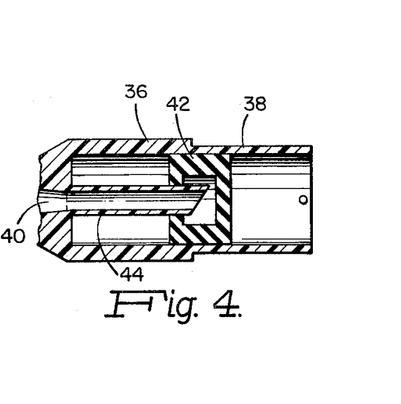
FIG. 4 is a fragmentary enlarged sectional view of one end of the female element.

The female body element 14 is characterized by a tapered portion 34 adapted to be inserted into and connect to standard tubing, so that the tapered portion 18 may be made a part of a blood bag, such as a blood-freezing or other sterilizing system employing tubing. The female body element 14 comprises also a knurled hand-grasping portion 36 and an insert tubular portion 38. A passageway 40 extends from the one to the other end of the female body element 14. Within the female passage 40 positioned from the one end of the female body element is a female septum 42 typically, but optionally, composed of a material similar to the male septum, the male septum 28 and the female septum of a resilient polymeric material and adapted to be punctured by the end of a hollow needle 44 which extends within the female passageway 40, one end of the needle adapted to pierce the septa 28 and 42, and the other end secured to a portion of the female passageway.

Figure 5:
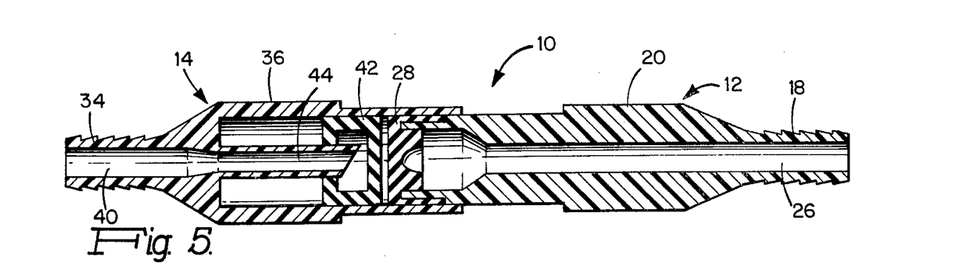
FIG. 5 is a cross-sectional view of the connector in the first extended position.

The female septum 42 is illustrated in a C form wherein the needle extends within the open portion of the C form and is spaced apart a slight distance from the interior wall of the septum 42, the female septum 42 providing a fluid-tight seal within the passageway and perferably positioned far enough back in the passageway to permit the insertion of the male body 12 within the interior of the tubular passageway 38, so that the connector 10 may be assembled as shown in FIG. 5 with a gap between the septa 28 and 42, or if desired, the septa may be in contact. The exterior surface of the tubular portion 38 contains an upwardly extended bayonet clasp 46 which fits into the vent and bayonet clasp channels 30 and 32 in the male body element, and provides means whereby the connector in the second engaged stage of its union may be secured together during use.

As illustrated, the female septum 42 is located in the female passageway 40, and is fitted snugly for slidable, fluid-tight movement therein. The male body element 12, and particularly the portions 22 and 24, is inserted within the passageway of tubular portions 36 and 38. The hollow needle 44 is positioned so that it can puncture both the septa 28 and 42 as the male and female body elements 12 and 14 are slid tightly together. The structure of the septum 42 is recessed back in the female body cavity so that the male body element can be inserted part way without the needle puncturing either septum. FIG. 5 illustrates the connector in the first extended stage of union. Since the connector is together, the mating septa 28 and 42 are protected from external contamination, but the systems to be joined together by the connector are not yet in fluid-flow communication, because the septa 28 and 42 in this first-stage union are intact.

Figure 12:
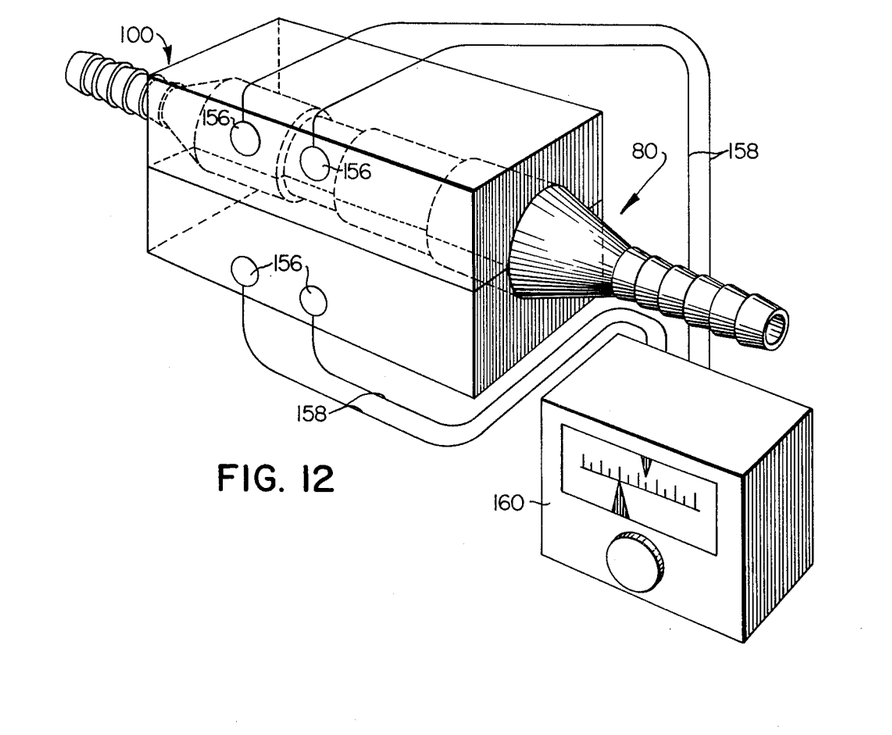
FIGS. 12 and 13 are perspective views of a heat sterilizer employed to sterilize my connector.
Figure 13:
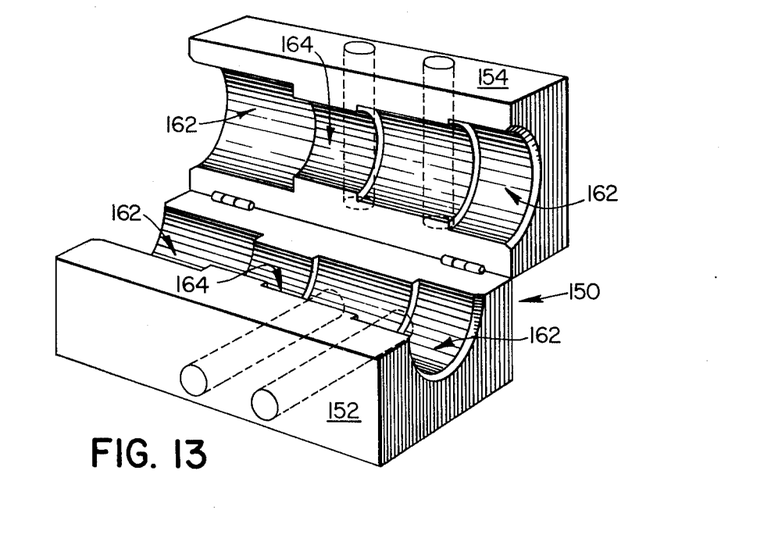

To insure sterility after the septa 28 and 42 are ruptured by the needle 44, the connector can be sterilized in a small dry heat-sterilizing oven, as illustrated more particularly in FIGS. 12–13; for example, a device which heats the connector to 350° F and holds that temperature for a time sufficient to ensure sterility, such as for about 10 minutes or more. Of course, it is recognized that other means of sterilizing the connector in the first extended stage of union may be employed, such as through chemical means, through the employment of ethylene oxide or other sterilizing gases, or liquid chemicals, or by heat, such as dry heat or steam, or by radiation, such as ultraviolet radiation, high-dosage gamma; for example, more than 2.5 megarads, or beta; for example, more than $3 \times 10^6$ volts, or by high-frequency radiation, such as through the use of microwaves, or other known sterilization techniques.

FIG. 5 shows a small vapor space or gap between the septa 28 and 42 when the connector is in the first stage of connection. The vent, which also serves as a bayonet-type channel 30 and 32, holds it into the male body element, allows excess vapor trapped between the septa 28 and 42 to escape. In a completely dry sterilization, air within the gap would be available to oxidize bacteria on the external septa surfaces.

Figure 6:
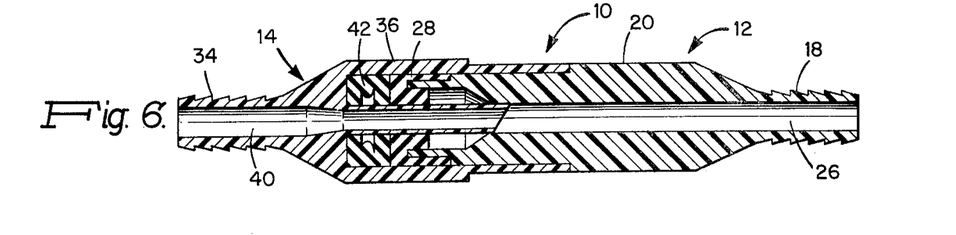
FIG. 6 is a view of the connection in the second engaged position.

In operation, when sterilization of the connector in its first extended stage of union, as illustrated in FIG. 5, is complete, the user or operator grasps the exterior knurled surfaces 26 and 36 of the male and female body elements, and pushes them firmly together, forcing the septum 42 in the female body element 14 back over the hollow needle 44, which needle also penetrates the septum 28 covering the end of the male body element. FIG. 6 illustrates my connector in the second engaged stage of the union. A bayonet-type clasp 46 holds the male and female parts of the connector securely together in the engaged stage of union. It is only at this time that the systems to be connected are finally joined by my connector. Since the septa surfaces 28 and 42 on my connector are heat-sterilized prior to puncture by needle 44, any possible contamination of the systems' being connected is thereby avoided.

Figure 7:
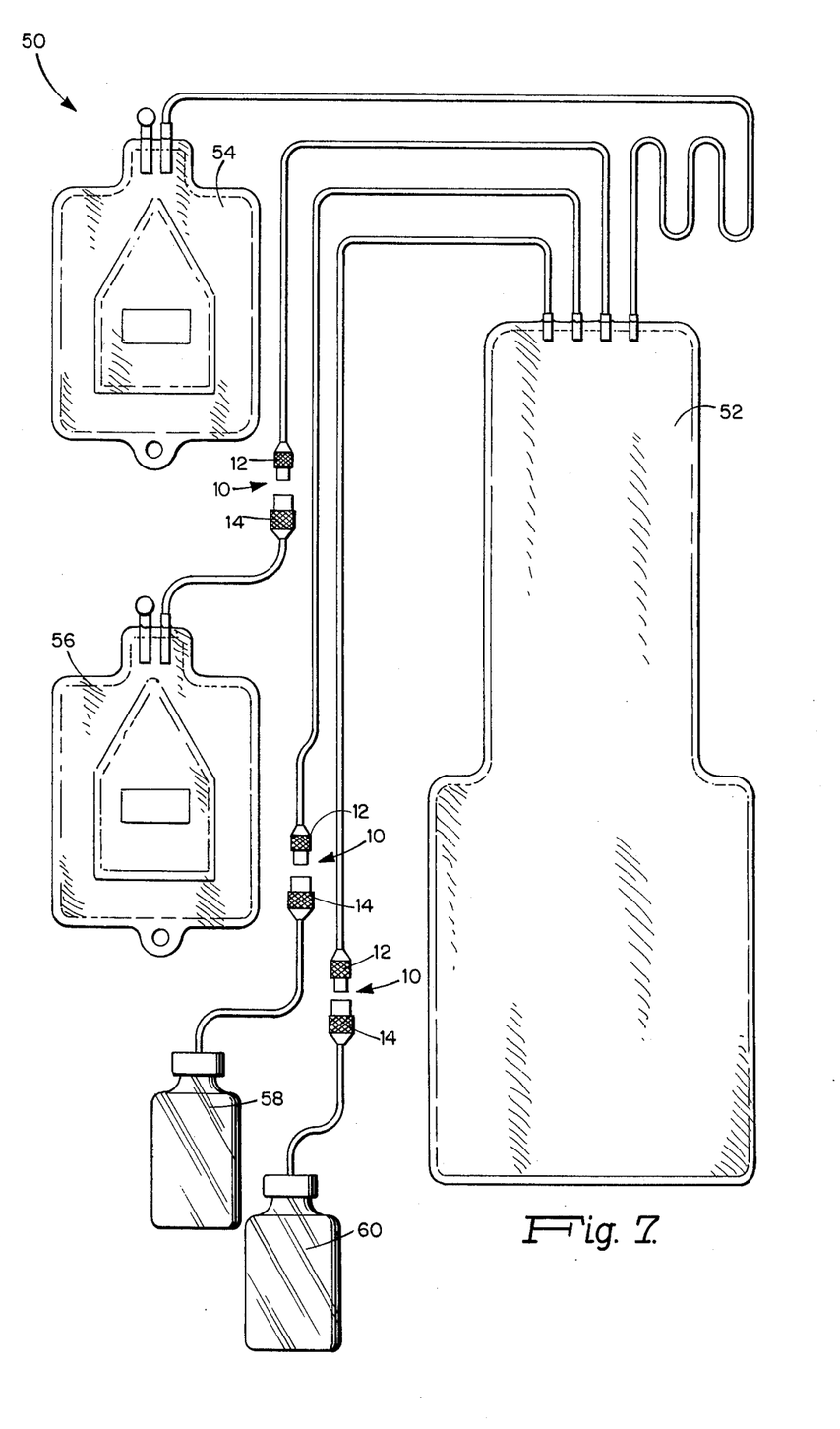
FIG. 7 is an illustration of the connector in a blood bag processing system.

One blood bag system 50 in which my connector 10 may be employed is illustrated in FIG. 7. The blood bag system comprises a frozen blood bag 52 and administration bag 54, a whole blood or donor blood bag 56, a cryo protective agent reservoir 58 and a rinsing or agglomeration solution reservoir 60, together with suitable tubing as shown. Typically, in such a system, my female body element 14 may be connected to reservoirs 56, 58 and 60, and male element 12 as shown connected to tubing to the frozen bag reservoir 52. In one example of a blood-processing system and method, whole or donor blood is collected in blood bag 56 and connection made by my connector to the frozen blood bag 52, so that the blood is transferred therein, and, thereafter, glycerol as a cryo protective agent would then be transferred from reservoir 58 through my connector into the frozen blood bag 52, and, thereafter, an agglomeration solution or rinsing solution would be transferred from reservoir 60 through my connector into blood bag 52. Similarly, after freezing and subsequent thawing, to separate the red cells from the plazma or the glycerol from the plazma, then the red cells would be transferred from bag 52 into the administration bag 54 for use by a recipient.

Figure 8:
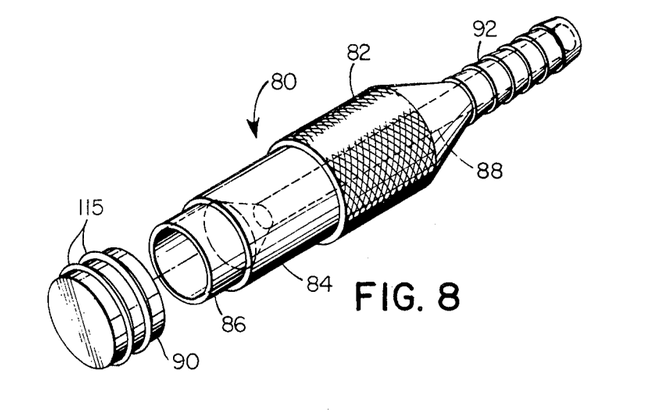
FIG. 8 is a perspective partially exploded view of another embodiment of the male element of my connector.
Figure 9:
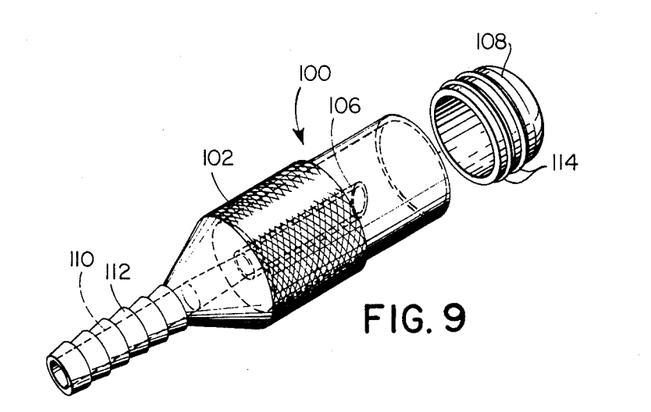
FIG. 9 is a perspective partially exploded view of another embodiment of the female element of my connector.

FIGS. 8 and 9 are perspective views of a modified embodiment of my connector wherein the male 80 and female 100 elements are illustrated with a different means to retain the elements together in the engaged position; to wit, without a mechanical clasping means, such as a bayonet-type clasp illustrated in FIGS. 1–7, to secure the elements together, and without a defined vent to permit the escape of air in the gap. Male element 80 includes: a knurled surface 82; tubular inset sections of reduced diameter 84 and 86; a passageway 88; a male septum composed of a polymeric cap element 90 and having two molded sealing 0 rings 115 on the external surface thereof; and a ridged surface to secure the septum to the end of the male element. Female element 100 includes: a knurled surface 102;

an extended reduced diameter section 104; a puncturing hollow needle 106; a passageway 112; and a female septum composed of a cup-like septum element 108 composed of a molded resilient needle-puncturable, sterilizable, polymeric material, and having two molded sealing 0 rings 114 on the external surface thereof.

Figure 10:
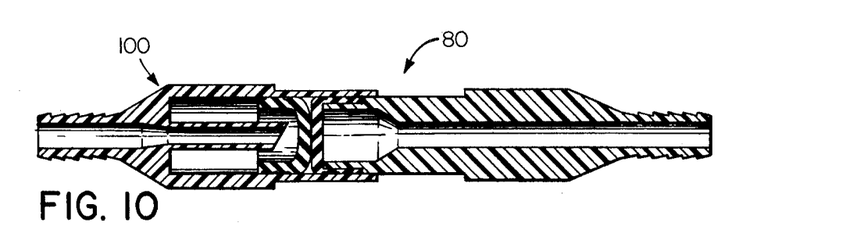
FIGS. 10 and 11 are cross-sectional views of the male and female elements of FIGS. 8 and 9 in an extended and engaged position, respectively.
Figure 11:
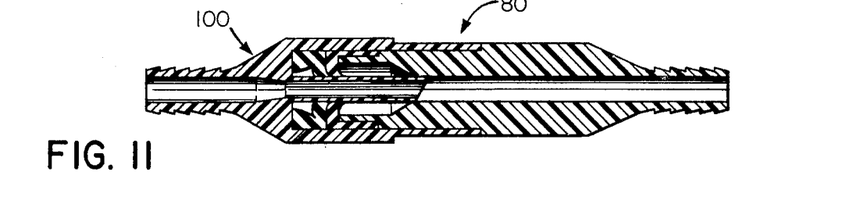

FIGS. 10 and 11 illustrate the embodiment of FIGS. 8 and 9 in the first extended and the second matingly engaged positions, respectively. In the embodiment illustrated, the elements 80 and 100 are very slightly tapered so that when the male element 80 is slidably engaged within the female element 100, it is secured together in the engaged position by galling or frictional forces due to the close fitting relationship. The male cap element 90 fits over the end of inset 86 in a snugly fitting manner, and is engaged in a fluid-tight manner with the interior wall of the female passageway by 0 rings 115. The male element may be engaged in a nonfluid-tight seal so that the need for a structural element to release any entrapped air in any gap between the septa is not required, although this is not the preferred embodiment as is hereinafter set forth.

The female septum 100 is formed of a molded polymeric material and is engaged in a fluid-tight slidable relationship within the interior of the inset section 104, so that it is moved backwardly by the male septum 80, and both are punctured by the needle 106 in the second engaged position. The female septum 108 is characterized by rounded or beveled shoulders so as to provide for the outward movement of the septum material when the septum 108 is punctured by the needle 106 as illustrated more particularly in FIG. 11.

FIGS. 12 and 13 are views of a heat sterilizer 150 having mating elements 152 and 154 hingedly connected together, and defining a generally tubular cavity with contoured mold surfaces 162 and 164, the cavity adapted to accept the blood connector elements; for example 100 and 80, but only in the first extended position. Contour 164 is two hemisphered raised sections of sufficient width to permit the male 80 and female 100 elements to be inserted into the closed sterilizer cavity at opposing ends, and to be coupled in the first extended, but not the second engaged, position during sterilization. The sterilizer includes electrical heating elements 156 in each element electrically connected 158 to a power source (not shown) and to a temperature controller and timer 160. The cavity of the sterilizer is defined when the elements 152 and 154 are close together and are contoured to fit, or be slightly larger than, the external dimensions of the tubular blood connector in the extended position, and to prevent the male 80 and female 100 elements from being slidably engaged in the matingly engaged position in the sterilizer. The peripheral undercut edges of the contoured section 164 abutts the edges of the knurled sections 82 and 102, so that the needle does not penetrate the female septum. The length of the reduced diameter section 164 is sufficient to correspond to the length between the respective edges of the reduced diameter sections of the connector in the extended position, but insufficient in length to permit the needle to puncture the septa. This length or the width of the section 164 may vary, depending upon the relative position of the elements of the connector.

In use, the male 80 and female 100 elements are inserted by the user into the respective open opposing ends of the closed sterilizer 150. The contoured cavity is designed as illustrated so that the user becomes aware if the elements are reversed or improperly positioned or placed. When the elements 80 nad 100 are properly inserted, they fit in the contoured cavity and extend generally equally from each end, or sufficient for each to be handled by the user, but cannot be inadvertently placed together in the engaged mating position due to the contoured ridges which hold the peripheral edges of the female and male elements apart. The connector is then heated for a time and to a temperature sufficient to sterilize the connector. For example, the sterilizer is heated to a temperature of 525° F for three minutes which raises the connector to a sterilizing temperature of at least about 400° F, which time and temperature are controlled and indicated to the user by element 160. The sterilizer is then opened as in FIG. 13 and the sterilized connector then removed for use as described. The sterilizer permits rapid and efficient sterilization of the connector just prior to use.

In the preferred embodiment of my invention, the male and female septa are engaged in a slidable fluid-tight manner in both the extended and engaged positions. It is necessary that the female septum always be so engaged; however, the male septum in one embodiment need not be fluid-tight. Where the male septum is not engaged in a fluid-tight manner and the connector after sterilization is not used shortly thereafter, the sterility of the connector is affected by the seepage of air in any gap left between the septa in the extended position.

In practice in the preferred embodiment, the user is furnished with the male and female elements, with the female septum positioned at the outer far end of its passageway. The user, when positioning the elements together in the extended position, then must place the face of the male septum into the female passageway and into the extended position, with the male and female septa facing then in contacting engagement, so that there is little or no air between the faces in the first extended position. After sterilization and on movement of the elements into the engaged position, then the sterilized air behind the female septum is pushed out through the needle and into the blood bag or other connecting source. Thus, air need not be entrapped between the faces of the female and male septa, and, depending on the type of coupling technique and male septum employed, no means to entrap air is required. In the preferred embodiment after sterilization and in the extended position, the connector remains sterilized.

My connector may be secured together in the engaged position by a number of different and various techniques. In addition, my sterilizer has been illustrated in connection with the sterilization of the connector with the use of elevated temperatures; that is, by the use of heat. However, it is recognized and is within the scope of my invention that sterilization may be effected by various other means within the sterilizer cavity, such as by the use of sterilizing liquids or gas or radiation.

My sterilizable connector and method have been illustrated to describe, for the purposes of illustration only, blood bag systems and the processing of frozen blood. However, it is recognized and is a part of my invention and discovery that my connectors may be used for a wide variety of intravenous and sterile solution transfers other than that expressly shown.

What I claim is:

1. A sterilizable connector for use in processing blood or other fluids, which connector comprises in combination:
   a. a male body element;
   b. a female body element;
   c. the male and female body elements adapted to be couplingly engaged in a first extended position, and, thereafter, in a matingly engaged position which permits the passage of fluid therethrough;
   d. means to secure the male and female body elements together when the elements are placed in the matingly engaged position;
   e. the male and female body elements each characterized by a coaxial passageway therethrough, the passageway having a one end and another end, one end of each element and passageway adapted to be connected to a connector or fluid source;
   f. a male septum at the other end of the male body element, the male septum resilient and adapted to be punctured by a needle, and the male septum closing in a fluid-tight manner the end of the male passageway at the other end, and slidably engaged in a fluid-tight manner with the interior surface of the female element;
   g. a female septum positioned within the female passageway a sufficient distance to permit the female and male body elements to be placed in a joined extended position, the female septum resilient and adapted to be punctured by a needle, and slidably engaged in a fluid-tight manner with the female passageway, the face surfaces of the septums being free of adhesive material;
   h. means to permit the escape of gas entrapped between the male and female septa when the male and female body elements are placed in a matingly extended position; and
   i. a septum-puncturing hollow needle element within the female body element passageway, the interior of the needle providing fluid-flow communication with the one end of the female body element passageway, whereby after sterilization of the connector and on movement by the user of the male or female body elements toward each other, the needle element punctures the male and female septa to provide a sterile fluid passageway through the connector, and the female septum is moved with the passageway so that the septa in the engaged position are in mating engagement.

2. The connector of claim 1 wherein the means to secure the male and female body elements together comprises a longitudinal bayonet-type channel extending along the exterior surface of the male body element, the female body element including an upwardly extending bayonet clasp from its external surface, the clasp adapted to engage the bayonet-type channel, and thereby to permit the male and female body elements to be placed in a matingly engaged secured position.

3. The connector of claim 2 wherein the means to permit the escape of gas in a gap between the septa includes a longitudinal channel extending along the exterior surface of the male or female body elements and into the gap between the septa.

4. The connector of claim 1 wherein the male septum comprises a cap-like element which is secured over the tubular other end of the male body element.

5. The connector of claim 4 wherein the male septum comprises a cap-like element composed of a sterilizable ploymer.

6. The connector of claim 1 wherein the female septum comprises a plug-like septum inserted into the female passageway a predetermined distance and which is composed of a sterilizable polymer.

7. The connector of claim 6 wherein the female septum comprises a C-type form, with the puncturing end of the needle element positioned within the open side of the C-type form, but spaced slightly apart from the septum wall when the male and female body elements are in an extended position.

8. The connector of claim 1 wherein the one and opposite ends of the male and female body elements are tapered down and adapted to be inserted within a plastic tubing.

9. The connector of claim 1 wherin the male and female body elements are composed of a conjectured, molded, medically accepted heat-resistant plastic material, and the male and female septa are composed of a silicone rubber-type material.

10. The connector of claim 1 wherein the main body portions of the male and female elements are characterized by a knurled hand-grasping exterior surface.

11. A blood bag system which comprises a processing bag and one or more reservoirs for the transfer of blood or an agglomerating solution to the blood bag, which system includes one or more connectors of claim 1 to provide for a sterile connector between such reservoirs, witih tubing between the reservoirs and the blood bag.

12. A two-stage sterilizable connector for use in processing blood, which connector comprises in combination:
   a. an elongated tubular male body element formed of a medically acceptable sterilizable polymer;
   b. an elongated tubular female body element formed of a medically acceptable sterilizable polymer;
   c. the male and female body elements adapted to be coupling engaged in a first extended position and in a second matingly engaged position;
   d. means to secure the male and female body elements together when the elements are in the second matingly engaged position;
   e. the male and female body elements each characterized by an elongated coaxial passageway therethrough, the elements having a one end and another end, one end of each element and passageway adapted to be connected to tubing or a fluid source;
   f. a polymeric male cap-like septum at the other end of the male body element, the male cap-like septum adapted to be punctured by a needle, the male cap closing in a fluid-tight manner the other end of the male passageway, and slidably engaged in a fluid-tight manner with the interior surface of the female element;
   g. a plug-like polymeric female septum positioned within the female passageway a sufficient distance to permit the male and female body elements to be placed in the first extended position, the female septum adapted to be punctured by a needle, and slidably engaged in a fluid-tight manner within the female passageway, whereby, in the first extended position, there is a gap between the septa, the face surfaces of the septums being free of adhesive material;
   h. a vent means to permit the escape of air entrapped in the gap between the male and female septa when the male and female body elements are moved from a first extended position into the second matingly engaged position; and i. a septum-puncturing thin hollow needle longitudinally positioned within the female body element passageway, the interior of the needle providing fluid-flow communication with one end of the female body element passageway, the other puncturing end of the needle positioned and spaced slightly apart from the wall of the female plug-like septum when the male and female body elements are in their first extended position, whereby after sterilization of the connector, when in the first extended position, and on movement by the user of the male and female body elements toward each other, the needle element punctures the male and female septa, and the female septum is pushed backwardly to place the male and female septa in a close fitting relationship, thereby providing a sterile fluid passageway through the male and female elements of the connector.

13. The connector of claim 12 wherein the male and female septa are composed of a silicone rubber material.

14. The connector of claim 12 wherein the vent means and the means to secure the male and female body elements together comprise a longitudinal bayonet J-type channel extending along the exterior surface of the male body element, the female body element including an upwardly bayonet clasp from its external surface, the clasp adapted to be engaged in the bayonet-type channel, and thereby to permit the male and female body elements to be secured in the second matingly engaged secured position.

15. The connector of claim 2 wherein the male septum is a polymeric capped element fitting over the other end of the male element, and includes a longitudinal channel on its exterior surface aligned with the exterior longitudinal channel of the male element, whereby gas entrapped in the gap between the septa, when the elements are moved from an extended to an engaged position, escapes through such channel.

16. The connector of claim 1 wherein the needle element extends from and coaxially with the passageway of the female element, the puncturing end of the needle element spaced apart from the female septum in the extended position, and extending into the coaxial passageway of the male element in the engaged position.

17. The connector of claim 1 wherein the connector is formed of a heat-sterilizable polymeric material, and the male and female septa are formed of the same puncturable heat-sterilizable material.

18. A sterilizable connector for use in processing blood or other fluids, which connector comprises in combination:
   a. a male body element;
   b. a female body element;
   c. the male and female body elements couplingly engaged in a first extended position, and, thereafter, in a second matingly engaged position which permits the passage of fluid therethrough;
   d. means to secure the male and female body elements together when the elements are placed in the matingly engaged position;
   e. the male and female body elements each characterized by a coaxial passageway therethrough, the passageway having a one end and another end, one end of each element and passageway adapted to be connected to a connector or fluid source;
   f. a male septum at the other end of the male body element; the male septum composed of a resilient material and adapted to be punctured by a needle, the male septum closing the end of the male passageway at the other end, and slidably engaged with the interior surface of the female element;
   g. a female septum closing the other end of the female passageway and positioned within the female passageway a sufficient distance to permit the female and male body elements to be placed in an extended position, the female septum composed of a resilient material and adapted to be punctured by a needle, and slidably engaged for movement in a fluid-tight manner within the female passageway, the face surfaces of the septums being free of adhesive material; and
   h. a septum-puncturing hollow needle element within the female body element passageway, the interior of the needle providing fluid-flow communication with the one end of the female body element passageway, whereby on movement of the male or female body elements toward each other from the extended position to the engaged position, the female septum is slidably moved by the male septum backwardly against the needle element, which punctures the male and female septa, and in the engaged position, provides a passageway through the connector.

19. The connector of claim 18 wherein the connector is composed of a heat-sterilizable polymeric material.

20. The connector of claim 18 wherein the male and female septa are composed of a heat-sterilizable silicone resin material.

21. The connector of claim 18 wherein the male septum is slidably engaged in a nonfluid-tight manner within the female passageway.

22. The connector of claim 18 wherein the male and female elements are contoured to secure the elements in a frictional interlocking relationship in the engaged position.

23. The connector of claim 18 which includes a locking means to secure the male and female elements together in the engaged position.

24. The connector of claim 18 wherein the female septum is a sterilizable polymeric cup-shaped element.

25. The connector of claim 18 wherein the female septum is a polymeric element having at least one circumferential extending ring on the outer surface thereof to form a fluid-tight slidable seal with the interior surface of the female element.

26. The connector of claim 18 wherein the female septum has a contoured cup-like form to permit the movement of the female septum material outwardly within the female passageway when the female septum is punctured by the needle element.

27. The connector of claim 18 wherein the male septum is engaged in a slidable fluid-tight manner within the passageway of the female element.

28. The connector of claim 27 wherein the male septum is composed of a polymeric material having at least one circumferentially extending ring on the outer surface thereof to form a fluid-tight slidable seal within the interior surface of the female element.

29. The connector of claim 18 wherein the faces of the male and female septa in the extended position are in contacting engagement.

30. A blood bag system which comprises a processing bag and one or more reservoirs with associated tubing for the transfer of blood or solutions, which system includes one or more of the connectors of claim 18 to provide for the transfer of blood or solutions.

31. A polymeric sterilizable connector for use in processing blood, which connector comprises in combination:
   a. an elongated tubular male body element formed of a sterilizable polymer;
   b. an elongated tubular female body element formed of a sterilizable polymer;
   c. the male and female body elements couplingly engaged in a first extended position and adapted to be engaged in a second matingly engaged position;
   d. means to secure the male and female body elements together when the elements are in the second matingly engaged position;
   e. the male and female body elements each characterized by an elongated coaxial passageway therethrough, the elements having a one end and another end, one end of each element and passageway adapted to be connected to tubing or a fluid source;
   f. a polymeric male septum enclosing the other end of the male body element, the male septum adapted to be punctured by a needle, the male septum closing in a fluid-tight manner the other end of the male passageway, and slidably engaged in a fluid-right manner with the interior surface of the female element;
   g. a polymeric female septum positioned within the female passageway in the first extended position, the female septum adapted to be punctured by a needle, and slidably engaged in a fluid-tight manner within the female passageway, the face surfaces of the septums being free of adhesive material; and
   h. a septum-puncturing needle longitudinally positioned within the female body element passageway, the interior of the needle providing fluid-flow communication with one end of the female body element passageway, the other puncturing end of the needle positioned and spaced slightly apart from the wall of the female septum in the first extended position, whereby after sterilization of the connector in the first extended position, and on movement of the male and female body elements toward each other, the needle element punctures the male and female septa, and the female septum is pushed backwardly to place the male and female septa in a close fitting relationship to provide a sterile fluid passageway through the connector.

32. The connector of claim 31 wherein the connector is formed of a heat-sterilizable polymeric material, and the male and female septa are formed of a puncturable heat-sterilizable polymeric material.

33. The connector of claim 31 wherein the male and female elements are tapered so as to provide a frictional inter-locking relationship when moved from a first extended to a second engaged position.

34. The connector of claim 31 wherein the male and female septa have faces which are in a close contacting relationship in the first extended position.

35. The connector of claim 31 wherein the male and female septa are composed of molded heat-sterilizable polymers subject to sterilization at temperatures of above about 400° F.

36. The connector of claim 31 wherein the male and female septa are composed of a molded resilient polymer, and have a plurality of mold 0-ring ridges about the external surfaces thereof to permit slidable movement in a fluid-tight manner.

* * * * *